US005340820A

United States Patent [19]

Gubin et al.

[11] Patent Number: 5,340,820

[45] Date of Patent: Aug. 23, 1994

[54] CYCLOAMINOALKOXYPHENYL DERIVATIVES, A PROCESS FOR THEIR PREPARATION AS WELL AS THE COMPOSITIONS CONTAINING THEM

[75] Inventors: Jean Gubin; Pierre Chatelain, both of Brussels; Jean Lucchetti, Chastre, all of Belgium

[73] Assignee: Elf Sanofi, Paris, France

[21] Appl. No.: 844,979

[22] Filed: Mar. 2, 1992

Related U.S. Application Data

[63] Continuation of Ser. No. 476,518, Feb. 7, 1990, abandoned.

[30] Foreign Application Priority Data

Feb. 7, 1989 [FR] France ................................ 89 01555

[51] Int. Cl.[5] .................... C07D 215/20; A61K 31/44

[52] U.S. Cl. ...................................... 514/300; 546/183

[58] Field of Search .......................... 546/183; 514/300

[56] References Cited

U.S. PATENT DOCUMENTS

| | | | |
|---|---|---|---|
| 3,859,305 | 1/1975 | Posselt et al. | 548/492 |
| 3,860,609 | 1/1975 | Lundt | 548/484 |
| 3,947,470 | 3/1976 | Brenner et al. | 549/468 |
| 3,991,060 | 11/1976 | Curran | 546/183 X |
| 4,103,012 | 7/1978 | Gubin et al. | 546/112 |
| 4,117,128 | 9/1978 | Brenner | 544/376 |
| 4,379,167 | 4/1983 | Lundsford et al. | 514/652 |
| 4,499,095 | 2/1985 | Rosseels et al. | 514/299 |
| 4,654,360 | 3/1987 | Greenhouse et al. | 514/418 |
| 4,675,405 | 6/1987 | Musser et al. | 546/172 |
| 4,826,847 | 5/1989 | Michel et al. | 514/256 |

FOREIGN PATENT DOCUMENTS

| | | |
|---|---|---|
| 0287696 | 10/1988 | European Pat. Off. . |
| 2341578 | 9/1977 | France . |

OTHER PUBLICATIONS

Alfred Burger, Chemical Structure and Biological Activity, pp. 64–80.

Chemical Abstracts, vol. 109, p. 606, 6405, 1988.

*Primary Examiner*—Johann Richter

*Assistant Examiner*—Catherine Scalzo

*Attorney, Agent, or Firm*—Wegner, Cantor, Mueller & Player

[57] ABSTRACT

Cycloaminoalkoxyphenyl derivatives useful for the treatment of certain pathological syndromes of the cardiovascular system and ocular diseases of formula:

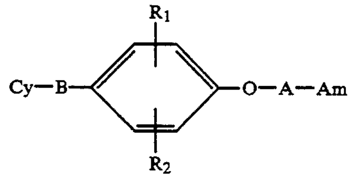

(1)

in which:

B represents a —S—, —SO— or —$SO_2$— group, $R_1$ and $R_2$, which are identical or different, each denotes hydrogen, a methyl or ethyl radical or a halogen such as chlorine, bromine or iodine, A denotes a straight or linear alkylene radical, having from 2 to 5 carbon atoms or a 2-hydroxypropylene radical in which the hydroxy is optionally substituted by a lower alkyl radical, Am denotes a group:

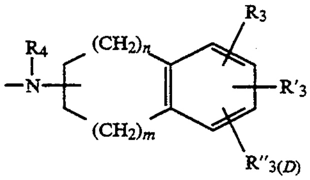

(D)

or

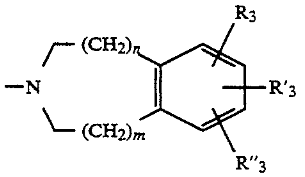

(E)

(Abstract continued on next page.)

in which: $R_3$, $R'_3$ and $R''_3$, which are identical or different, each denotes hydrogen, a halogen atom such as chlorine or bromine, a lower alkyl group or a lower alkoxy group, $R_4$ denotes hydrogen or an alkyl radical,
n and m, identical or different, each denotes 0, 1, 2 or 3,
Cy represents a group of formula:
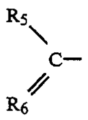
(F)
or
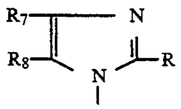
(G)
pharmaceutically acceptable salts thereof.
13 Claims, No Drawings

CYCLOAMINOALKOXYPHENYL DERIVATIVES, A PROCESS FOR THEIR PREPARATION AS WELL AS THE COMPOSITIONS CONTAINING THEM

This application is a continuation of U.S. application Ser. No. 07/476,518 filed Feb. 7, 1990 abandoned.

In a general manner, the present invention relates to new cyclic derivatives and, in particular, to new cycloaminoalkoxyphenyl derivatives as well as to a process for their preparation.

More particularly, the new cycloaminoalkoxyphenyl derivatives of the invention may be represented by the general formula:

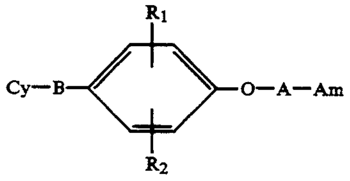

(1)

in which:

B represents a —S—, —SO— or $—SO_2—$ group, $R_1$ and $R_2$, which are identical or different, each denotes hydrogen, a methyl or ethyl radical or a halogen such as chlorine, bromine or iodine, A denotes a straight or linear alkylene radical, having from 2 to 5 carbon atoms or a 2-hydroxypropylene radical in which the hydroxy is optionally substituted by a lower alkyl radical, Am denotes a group:

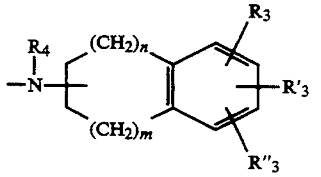

(D)

or

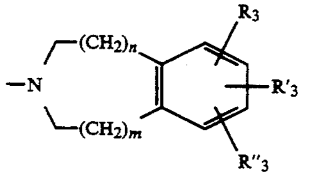

(E)

in which:

$R_3$, $R'_3$ and $R''_3$, which are identical or different, each denotes hydrogen, a halogen atom such as chlorine or bromine, a lower alkyl group or a lower alkoxy group, $R_4$ denotes hydrogen or an alkyl radical, n and m, identical or different, each denotes 0, 1, 2 or 3, Cy represents a group of formula:

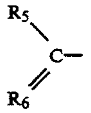

(F)

or

-continued

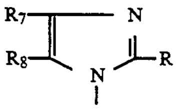

(G)

R denotes hydrogen, an alkyl radical, a cycloalkyl radical, a benzyl radical or a phenyl radical optionally substituted by one or more substituents, which may be identical or different, selected from halogen atoms, for example fluorine, chlorine or bromine or from lower alkyl groups, lower alkoxy groups or nitro groups, $R_5$ and $R_6$ are taken together with the carbon atom to which they are attached to form:

an optionally aromatic mono- or oi-cyclic carbocyclic group having from 5 to 10 carbon atoms and optionally substituted by a R group in the α-position with respect to the methyne group, an optionally aromatic 5-membered heterocyclic group, the heteroatoms or heterogroups being selected from the groups O, S, N, N—$R_9$; O and N; O and N—$R_9$; S and N; S and N—$R_9$; N and N; N and N—$R_9$; the heterocyclic group being optionally substituted by a R group in the α-position with respect to the methyne group and optionally substituted by one or two groups selected from lower alkyl and phenyl groups, an optionally aromatic 6- to 10-membered mono- or hi-cyclic group, the heteroatoms or heterogroups being selected from the groups O,S, N, N—$R_9$, O and N; O and N—$R_9$; S and N; S and N—$R_9$; N and N; N and N—$R_9$, the heterocyclic group being optionally substituted by a R group in the α-position with respect to the methyne group, $R_7$ and $R_8$, which are identical or different, each denotes hydrogen, a lower alkyl radical or a phenyl radical or when they are taken together with the carbon atoms to which they are attached, represent an optionally aromatic 6-membered carbocyclic ring, $R_9$ denotes hydrogen, a lower alkyl, phenyl, benzyl or halogenobenzyl group.

In the present context, both in the description and in the Claims, the following meanings attach to the terms stated above: "alkyl" denotes straight or branched saturated aliphatic hydrocarbon residues having up to 8 carbon atoms, such as methyl, ethyl, n-propyl, isopropyl, n-butyl, isobutyl, tert-butyl, n-pentyl, neopentyl, n-hexyl, n-heptyl or n-octyl, "lower alkyl" denotes straight or branched saturated hydrocarbon residues having up to 4 carbon atoms, such as methyl, ethyl, n-propyl, isopropyl, n-butyl, iso-butyl, tert-butyl or 1-methylpropyl, "lower alkoxy" denotes a hydroxy group substituted with a lower alkyl group as defined above, "cycloalkyl" denotes an alicyclic group having from 3 to 6 carbon atoms, such as cyclopropyl or cyclohexyl.

Thus, taking into account the meanings given above:

R can denote, in particular, a methyl, ethyl, n-propyl, isopropyl, n-butyl, isobutyl, tert-butyl, 1-methylpropyl, n-pentyl, neopentyl, phenyl, monofluoro-, monochloro- or monobromophenyl, difluoro-, dichloro- or dibromophenyl, monomethyl- or dimethylphenyl, monomethoxy- or dimethoxyphenyl radical, a methylphenyl radical substituted by a halogen atom or a cyclopropyl or cyclohexyl radical, $R_3$ $R'_3$ and $R''_3$ denote in particular, a methyl or methoxy radical or a chlorine atom, $R_4$ represents, in particular, a methyl, ethyl, n-propyl, isopropyl, n-butyl, isobutyl, tert-butyl, n-pentyl, neopentyl, n-hexyl, n-heptyl or n-octyl radical, A denotes, in particular, a 1,2-ethylene, 1,3-propylene, 2-methyl-1,3-propylene, 1,4-tetramethylene or 1,5-pentamethylene chain, Cy denotes, in particular, a phenyl, cyclohexenyl, indenyl, naphthyl, dihydronaphthyl, pyridyl, dihydropyridyl, furyl, dihydrofuryl, thienyl, dihydrothienyl, pyrrolyl, dihydropyrrolyl, pyrazolyl, imidazolyl, pyrimidyl, pyrazinyl, pyridazinyl, oxazolyl, isoxazolyl, thiazolyl, benzofuryl, benzothienyl, indolyl, benzimidazolyl, benzoxazolyl, quinolinyl, benzisoxazolyl, cinnolinyl, quinoxalinyl, quinazolinyl, indolizinyl, thienopyridyl, tetrahydrothienopyridyl, pyrrolopyridyl, pyrazolo-pyridyl, pyrrolopyridazinyl, imidazopyridyl group.

A particular class of compounds of formula (1) are those in which Cy represents a indolizinyl, benzofuryl, benzothienyl, indolyl, oxazolyl, pyrazolyl, phenyl, pyrazolo [1,5-a] pyridyl or imidazo [1,2-a] pyridyl group.

Another class of compounds of the invention may be denoted by the formula (1) in which $R_1$ and $R_2$ each denotes hydrogen.

As particularly valuable compounds of formula (1) there may also be mentioned those in which $R_3$ $R'_3$ and $R''_3$ denote hydrogen or methoxy.

Other valuable compounds of formula (1) are those in which R represents an isopropyl or cyclopropyl group.

The invention also relates to the pharmaceutically acceptable salts of the compounds of formula (1) formed with an organic or inorganic acid.

As examples of organic salts of this type, there may be mentioned the oxalate, maleate, fumerate, methanesulfonate, benzoate, ascorbate, pamoate, succinate, hexamate, bismethylenesalicylate, ethanedisulfonate, acetate, propionate, tartrate, salicylate, citrate, gluconate, lactate, malate, cinnamate, mendelate, citraconate, aspartate, palmitate, stearate, itaconate, glycolate, p-aminobenzoate, glutamate, benzenesulfonate and theophyllineacetate, as well as the salts formed with an amino acid such as the lysine or histidine salt.

As examples of inorganic salts of this type, the hydrochloride, hydrobromide, sulfate, sulfamate, phosphate and nitrate may be mentioned.

The compounds of formula (1) can exist, in some cases in the form of optical isomers, in particular as a result of the asymmetric carbon present when A represents a 2-hydroxypropylene chain.

The invention relates, at the same time, to all of the isomers of the compounds of formula (1), isomers considered in the dextrorotatory or laevorotatory form, or in the form of a mixture, for example in the form of a racemic mixture.

It has been found that the compounds of the invention possess exceptional pharmacological properties, especially calcium transport inhibitory properties, as well as bradycardiac, hypotensive and antiadrenergic properties.

From this point of view, the preferred compounds of the invention are those in which B represents a $-SO_2-$ group.

These properties are capable of making the compounds in question very useful in the treatment of certain pathological syndromes of the cardiovascular system, especially in the treatment of angina pectoris, hypertension, arrhythmia and cerebral circulatory insufficiency.

In the antitumour field, the compounds of the invention may be useful as potentiators of anticancer drugs.

Depending on the route of administration selected, the daily dosage for a human being weighing 60 kg will be between 2 and 500 mg of active principle.

Similarly, it will be possible to use the compounds of the invention alone or in combination with an anti-inflammatory agent in order to reduce and/or control excessive intraocular pressure.

To this effect, it will be possible to use the compounds of the invention for the treatment of pathological ocular diseases, in particular in the treatment of glaucoma.

Generally, from 5 ng to 0.5 mg of active principle according to the invention will be administered to each eye, the daily frequency of administration depending on the gravity of the disease to be treated.

Consequently, the invention also relates to pharmaceutical or veterinary compositions containing as active principle at least one compound of formula (1) or a pharmaceutically acceptable salt of this derivative in combination with a pharmaceutical vehicle or appropriate excipient.

The compounds of the invention may be obtained as follows:

The compounds of formula I in which B represents a $-S-$ or $-SO_2-$ group and A represents an alkylene radical may be prepared, according to the invention, by condensing in the presence of an acid acceptor and in a polar solvent such as dimethylsulfoxide or an alcohol, for example butanol, or a ketone such as methyl ethyl ketone, or a non-polar solvent such as an aromatic hydrocarbon, for example benzene, toluene or xylene, a 4-alkoxyphenyl derivative of general formula:

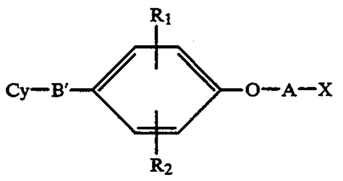

(2)

in which B' represents a $-S-$ or $-SO_2-$ group, Cy, $R_1$ and $R_2$ have the same meaning as above, A represents an alkylene radical as defined in the formula (1) and X represents a halogen atom, preferably bromine, or an alkylsulfonyloxy group having from 1 to 4 carbon atoms such as for example, methanesulfonyloxy, or an arylsulfonyloxy group having from 6 to 10 carbon atoms, such as benzenesulfonyloxy or p-toluenesulfonyloxy, with an amine of general formula:

H-Am (3)

in which Am has the same meaning as above, in order to form the desired derivative of formula (1) in the form of the free base.

In general, the condensation in question is performed at a temperature between room temperature and the refluxing temperature of the medium, the acid acceptor being, for example, an alkali metal carbonate or hydroxide or an excess of amine of formula (3).

The compounds of formula (2) in question can be obtained:

a) when X is a halogen, by condensation of a 4-hydroxyphenyl derivative of general formula:

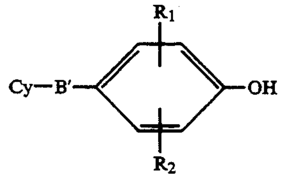
(4)

in which Cy, B′, $R_1$ and $R_2$ have the same meaning as above, with a dihaloalkane of general formula:

Hal-A-Hal (5)

in which A denotes an alkylene radical as defined in formula (1) and Hal denotes a halogen atom, preferably bromine, this reaction being performed at reflux in a solvent such as methyl ethyl ketone or N,N-dimethylformamide and in the presence of a basic agent such as an alkali metal carbonate, for example potassium carbonate, an alkali metal hydride such as sodium hydride, an alkali metal hydroxide, for example sodium or potassium hydroxide, or an alkali metal alcoholate, for example sodium methylate or ethylate, b) when X denotes an alkylsulfonyloxy or arylsulfonyloxy group, by condensation of a halide of general formula:

Hal-W in which W represents an alkylsulfonyl radical having from 1 to 4 carbon atoms, for example methanesulfonyl, or an arylsulfonyl radical having from 6 to 10 carbon atoms, for example benzenesulfonyl or p-toluenesulfonyl, in an acid acceptor solvent, for example pyridine, with a 4-hydroxyalkoxy derivative of general formula:

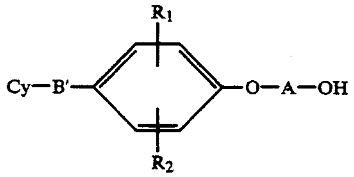
(6)

in which Cy, B′, $R_1$ and $R_2$ have the same meaning as above and A denotes an alkylene radical as defined in formula (1).

As regards the compounds of formula (6), these can be prepared by condensing, in a suitable solvent such as N,N-dimethylformamide and in the presence of a basic agent such as an alkali metal carbonate, for example potassium carbonate, an alkali metal hydroxide such as sodium or potassium hydroxide, an alkali metal hydride such as sodium hydride or an alkali metal alcoholate, for example sodium methylate or ethylate, an indolizine derivative of formula (4) above, with a halogenated alcohol of general formula:

Hal-A-OH (7)

in which A denotes an alkylene radical as defined in the formula (1) and Hal has the same meaning as above.

The amines of formula (3) are known compounds having been described in the European patent applications No. 219.813 and 227.986 or can be prepared according to the methods described therein.

Some compounds of formula (4) are known compounds, for example those in which Cy represents a benzofuryl or benzothienyl group and B′ represents a $—SO_2—$ group (U.S. Pat. No. 4,117,128) or in which Cy represents a 1-indolizinyl group (EP application No. 235.111).

In general, the other compounds of formula (4) can be prepared by adapting to the desired compound of the method described in the aforementioned US patent or the methods described below.

In most cases, the compounds of formula (4) can be obtained from a benzenesulfonyl or phenylthio group, this group being O-protected at position 4.

The group in question is fixed to the appropriate heterocycle or carbocycle using a Friedel-Crafts reaction and the oxygen at position 4 of the benzenesulfonyl or phenylthio group is deprotected by means of standard procedures in order to regenerate the hydroxyl group.

Below are given examples of methods commonly used for preparing derivatives of formula (4):

Compounds of formula (4) in which Cy represents a (F) group.

1) The compounds of formula (4) in which Cy represents a 2-R-indolizin-3-yl group can be prepared by reacting an indolizine derivative of general formula:

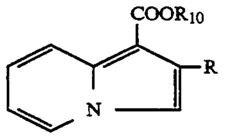
(8)

in which R has the same meaning as above and $R_{10}$ represents a lower alkyl radical, preferably ethyl, with a halide of general formula:

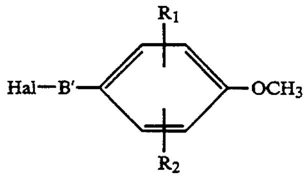
(9)

in which B′, $R_1$, $R_2$ and Hal have the same meaning as above and in the presence of a Friedel-Crafts catalyst such as aluminium chloride to provide a compound of general formula:

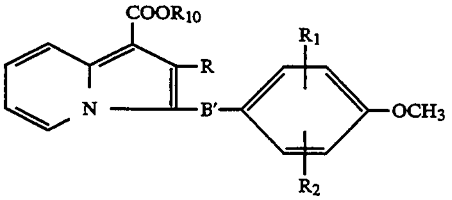

(10)

in which B′, R, $R_1$, $R_2$ and $R_{10}$ have the same meaning as above. The compound of formula (10) is subsequently demethylated using an ethanethiol-/aluminium chloride mixture in order to form the 4-methoxyphenyl derivative of general formula:

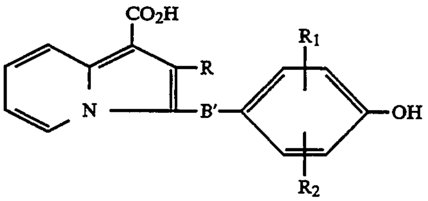

(11)

in which B′, R, $R_1$ and $R_2$ have the same meaning as above which, when heated to about 200° C. provides the required compound of formula (4).

The compounds of formula (8) are either known compounds having been published in J. Chem. Soc. 1962 pp. 2627–2629 or compounds which can be prepared in accordance with the method described therein.

2) The compounds of formula (4) in which Cy represents a 2-R-imidazo [1,2-a] pyrid-3-yl group can be prepared by reacting a 2-R-imidazo [1,2-a] pyridine with a halide of formula (9) in the presence of a Friedel-Crafts catalyst such as aluminium chloride to provide a compound of general formula:

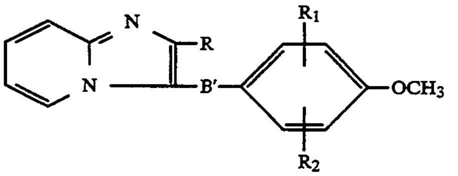

(12)

in which B′, R, $R_1$ and $R_2$ have the same meaning as above The compound of formula (12) is subsequently demethylated using an appropriate agent, for example hydrobromic acid or an ethanethiol-/aluminium chloride mixture to give the required compound of formula (4).

Some 2-aryl-imidazo [1,2-a] pyridines are known from J. Med. Chem 8. p. 305 (1965). The other 2-R-imidazo [1,2-a] pyridines can be obtained in accordance with the methods described in the aforementioned reference or by using standard procedures. Alternatively, the compounds of formula (12) can be obtained from a 2-R-3-halo-imidazo[1,2-a] pyridine and an alkali metal salt of a 4-methoxy derivative of formula (15).

3) The compounds of formula (4) in which Cy represents a pyridyl or 3-R-4-pyridyl group can be obtained by demethylating with an appropriate agent such as aqueous hydrobromic acid, a 4-methoxyphenyl derivative of general formula:

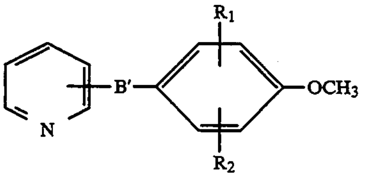

(13)

or

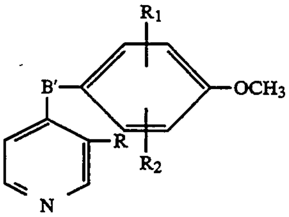

(13′)

in which B′, $R_1$ and $R_2$ have the same meaning as above and R has the same meaning as above with the exception of hydrogen, to provide the required compounds of formula (4). The compounds of formulae (13) and (13′) in which B′ represents a $-SO_2-$ group can be prepared by oxidizing a sulfide derivative of general formula:

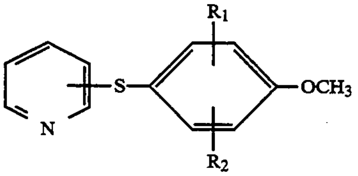

(14)

or

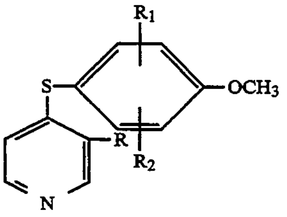

(14′)

in which $R_1$ and $R_2$ have the same meaning as above and R has the same meaning as in formula (13) or (13′).

Some compounds of formula (14) are known compounds having been described in the U.S. Pat. No. 4,128,552. The other compounds of formula (14) can be obtained in accordance with the method described in the aforementioned US patent. As for the compounds of formula (14′), they can be prepared from a 3-R-pyridine in which R is other than hydrogen, by oxidation with hydrogen peroxide in acetic acid to provide the corresponding 3-R-pyridine-N-oxide derivative which is reacted with a nitric acid/sulfuric acid mixture to give the corresponding 3-R-4-nitro-pyridine-N-oxide derivative.

This nitro derivative is then first reacted with acetyl bromide, then with iron powder in acetic acid to give the corresponding 3-R-4-bromo-pyridine which, when treated with a thiophenol derivative of general formula:

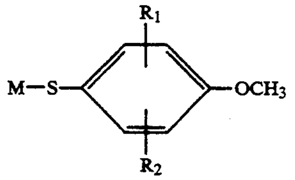

(15)

in which $R_1$ and $R_2$ have the same meaning as above and M represents an alkali metal atom such as sodium, provides the required compound of formula (14').

4) The compounds of formula (4) in which Cy represents a 2-R-quinolin-3-yl group can be prepared by reacting an α-haloketone of general formula:

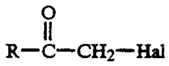

(16)

in which R and Hal have the same meaning as above, with a metal derivative of general formula:

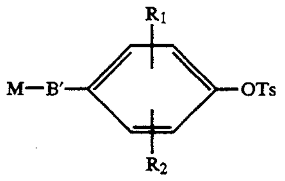

(17)

in which M, B', $R_1$ and $R_2$ have the same meaning as above and Ts represents a p-toluenesulfonyl group, to provide a ketone of general formula:

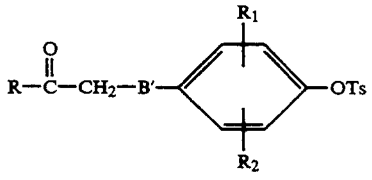

(18)

in which B', R, $R_1$, $R_2$ and Ts have the same meaning as above. This ketone of formula (18), when treated with 2-amino-benzaldehyde Helv. Chem. Act. vol. XVIII, p. 1235 (1935) gives the 4-methoxyphenyl derivative of general formula:

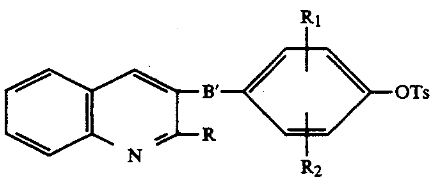

(19)

in which B', R, $R_1$, $R_2$ and Ts have the same meaning as above, which is subsequently hydrolysed in basic medium, for example in an aqueous alkali metal hydroxide, to give the required compound of formula (4).

5) The compounds of formula (4) in which Cy represents a 3-R-cinnolin-4-yl of 4-R-cinnolin-3-yl group can be prepared by reacting a 3-R-4-halogeno-cinnoline (J. Chem. Soc. 1953, p. 609), with a thiophenol derivative of general formula:

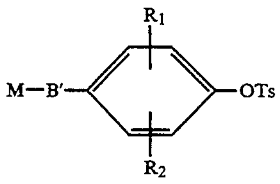

(20)

in which M, $R_1$, $R_2$ and Ts have the same meaning as above and B' represents a —S— group to provide the 4-tosyloxyphenyl derivative of general formula:

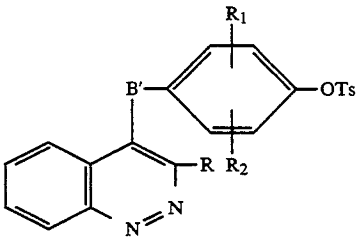

(21)

or

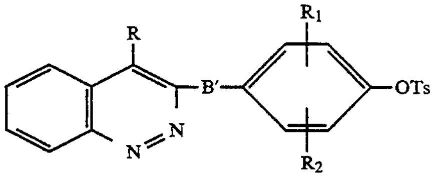

(21')

in which R, $R_1$, $R_2$ and Ts have the same meaning as above and B' represents a —S— group.

The 4-tosyloxyphenyl derivative of formula (21) or (21') is subsequently hydrolysed in basic medium, for example in an aqueous alkali metal hydroxide, to give the required compound of formula (4) in which B' represents a —S— group. Compounds of formula (20), in which —OTs is replaced by $—OCH_3$, can also be used. In this case, the compound corresponding to formula (21) or (21') is demethylated by means, for example, of hydrobromic acid.

When oxidized with a suitable agent such as hydrogen peroxide in acetic acid or potassium permanganate, the sulfide of formula (21) or (21') produces the compound of formula (21) or (21') in which B' represents a $—SO_2—$ group, which compound after hydrogenation on a catalyst such as palladium charcoal or platinum black gives the required compound of formula (4) in which B' represents a $—SO_2—$ group.

Alternatively, the compounds of formula (4) in question in which B' represents a $—SO_2—$ group can be obtained from a 3-R-4-halogeno-cinnoline or a 4-R-3-halogeno-cinnoline by reacting this compound with a benzenesulfonyl derivative of formula (20) in which B' represents a $—SO_2—$ group to form a compound of formula (21) or (21') in which B' represents a $—SO_2—$ group which is detosylated as described above to provide the required compound of formula (4).

6) The compounds of formula (4) in which Cy represents a 6-R-pyrrolo [1,2-b] pyridazin-5-yl group can be prepared by reacting a 3-halogenomethylpyridazine with a metal derivative of formula (17) to form a pyridazine derivative of general formula:

(22)

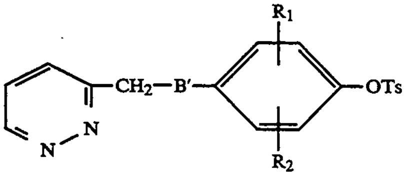

in which B', $R_1$, $R_2$ and Ts have the same meaning as above which is subsequently reacted with an α-haloketone of formula (16) in the presence of a non-nucleophlic base such as, for example, 1,8-diazabicyclo[5,4,0 ] undec-7-ene to give the pyrrolo[1,2-b] -pyridazine derivative of general formula:

(23)

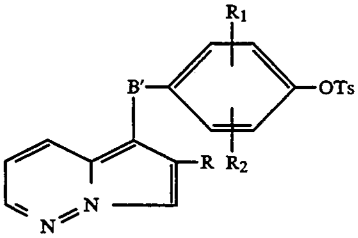

in which B', R, $R_1$, $R_2$ and Ts have the same meaning as above.

The tosyl derivative of formula (23) is then hydrolysed in a basic medium, for example, in an aqueous alkali metal hydroxide, to give the required compound of formula (4).

3-Chloromethyl-pyridazine is a known compound having been published in Khim. Geterot. Sikl. Soedin. 3, pp. 412–414 (1970).

7) Compounds of formula (4) in which Cy represents a 2-R-pyrazolo [1,5-a]pyrid-1-yl group can be prepared in accordance with the method described in the European patent application No. 121.197, by treating a 2-R-pyrazolo[1,5-a]pyridine with a halide of formula (9) in the presence of a Friedel-Crafts catalyst such as, for example, aluminium chloride, to provide the 4-methoxyphenyl derivative of general formula:

(24)

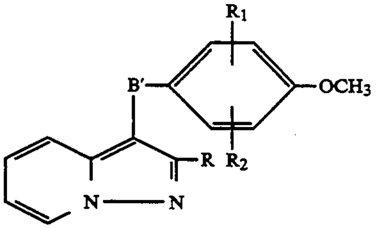

in which B', R, $R_1$ and $R_2$ have the same meaning as above.

The pyrazolopyridine derivative of formula (24) is then demethylated by using, for example, pyridine hydrochloride at 200°–220° C. to give the required compound of formula (4).

8) The compounds of formula (4) in which Cy represents a phenyl group can be prepared by reacting benzene with a halide of formula (9) in the presence of a Friedel-Crafts catalyst such as aluminium chloride to give the required compound of formula (4).

9) The compounds of formula (4) in which Cy represents a 2-R-phenyl group or a 1-R-2-naphthyl group can be prepared by treating a halide of general formula:

(25)

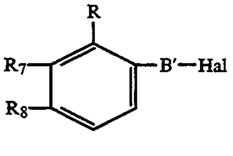

in which B', R and Hal have the same meaning as above and $R_7$ and $R_8$ each represents hydrogen or are taken together with the carbon atom to which they are attached to form a phenyl group, with a methoxyphenyl derivative of general formula:

(26)

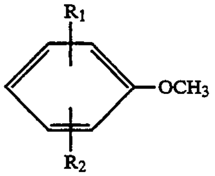

in which $R_1$ and $R_2$ have the same meaning as above, in the presence of a Friedel-Crafts catalyst such as aluminium chloride, to give the compounds of general formula:

(27)

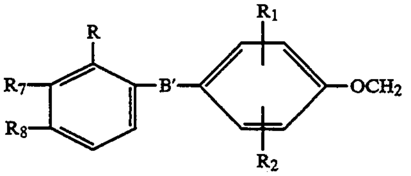

in which B', R, $R_1$ and $R_2$ have the same meaning as above and $R_7$and $R_8$ have the same meaning as in formula (25).

The compounds of formula (27) are then demethylated using, for example, aqueous hydriodic acid to provide the required compound of formula (4).

Some compounds of formula (25) are known compounds having been described in C.A. 81, 63285g, or can be obtained in accordance with known procedures.

Alternatively, the compounds of formula (27) in which $R_7$and $R_8$ each represents hydrogen and B' represents a $—SO_2—$ group can be prepared by treating the alkali metal derivative of a 2R-benzenesulfonate with a phenyl derivative of formula (26) in the presence of methanesulfonic acid/phosphorous pentoxide, according to the method described in Communications, April 1984, p. 323.

In accordance with another procedure, the compounds of formula (4) in which Cy represents a 2-naphthyl group and B' represents a $—SO_2—$ group can be obtained by reacting a 2-halogenosulfonyl naphthalene with a $R_1R_2$-phenol derivative. This sulfonate derivative is then rearranged in the presence of aluminium chloride in order to form a complex which is treated with an acid such as hydrochloric acid in order to form the required compound of formula (4).

10) The compounds of formula (4) in which Cy represents an optionally mono- or di-substituted 2-R-4,5-dihydro-furan-3-yl group can be prepared by heating a ketone derivative of formula (18) with a 1,2-dihalogenoethane of general formula:

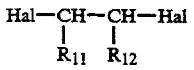

(28)

in which $R_{11}$ and $R_{12}$, which are identical or different, each represents hydrogen, a lower alkyl radical or a phenyl radical, in the presence of a basic reagent such as an alkali metal carbonate, in order to form a cyclopropane derivative of general formula:

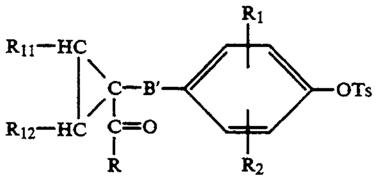

(29)

in which B', R, $R_1$, $R_2$, $R_{11}$, $R_{12}$ and Ts have the same meaning as above.

The cyclopropane derivative of formula (29) is then heated between 100° and 130° C. in the presence of a phase transfer catalyst such as, for example, triphenylphosphine or tricaprylylmethyl ammonium chloride to provide the 4-tosyloxyphenyl derivative of general formula:

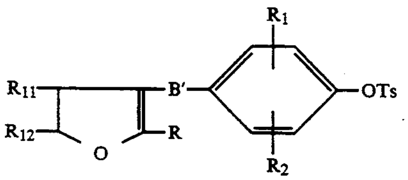

(30)

in which B', R, $R_1$, $R_2$, $R_{11}$, $R_{12}$ and Ts have the same meaning as above, and the said 4-tosyloxyphenyl derivative is detosylated by treatment with a basic agent such as an alkali metal hydroxide in order to give the required compound of formula (4).

11) The compounds of formula (4) in which Cy represents a mono- or di-substituted 2-R-furan-3-yl group can be obtained by oxidizing, for example, with manganese oxide, a 4,5-dihydrofuran derivative of formula (30) to form a furan derivative of general formula:

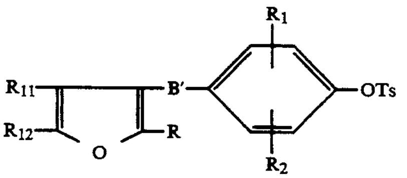

(31)

in which B', R, $R_1$, $R_2$, $R_{11}$, $R_{12}$ and Ts have the same meaning as above, which furan derivative is subsequently treated with a basic agent such as an alkali metal hydroxide to form the required compound of formula (4).

12) The compounds of formula (4) in which Cy represents a 2-R-furan-3-yl or a 2-R-thien-3-yl or a 2-R-pyrrol-3-yl group can be prepared by reacting a compound of general formula:

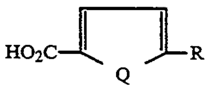

(32)

in which R has the same meaning as above and Q represents —O, —S or —N—$R_9$, with a halide of formula (9) and in the presence of a Friedel-Crafts catalyst such as aluminium chloride, to give a 4-methoxy derivative of general formula:

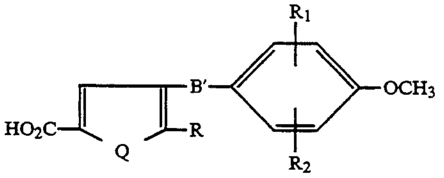

(33)

in which B',R, $R_1$, $R_2$ and Q have the same meaning as above, which is subsequently decarboxylated by heating and then demethylated with a suitable agent such as pyridine hydrochloride or hydrobromic acid in order to give the required compound of formula (4).

Alternatively, the compounds of formula (4) in which Cy represents an optionally substituted 2-R-furan-3-yl group can prepared by oxidation, for example by means of manganese oxide, of a sulfide derivative of formula (30) to form a 2-R-3-(4-tosyloxybenzenesulfonyl)furan derivative which is subsequently treated by a basic medium, for example a metal alkali hydroxide, to give the required compound of formula (4)

13) The compounds of formula (4) in which Cy represents a 1-R-imidazol-2-yl or a 1-R-benzimidazol-2-yl group can be obtained by reacting a 1-R-imidazole of a 1-R-benzimidazole with a halide of formula (9) in the presence of a Friedel-Crafts catalyst such as aluminium chloride to form a compound of general formula:

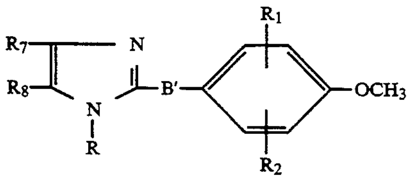

(34)

in which B', R, $R_1$ and $R_2$ have the same meaning as above, $R_7$ and $R_8$ each represents hydrogen or are taken together with the carbon atoms to which they are attached to form a phenyl group, which compound is then demethylated using an ethanethiol/aluminium chloride mixture in the presence of sodium hydride in order to form the required compound of formula (4).

Compounds of formula (34) in which the —$OCH_3$ group is replaced by a —O— benzyl group can also be used. In this case, the compounds of formula (34) in question are debenzylated using hydrogen and a suitable catalyst, for example palladium on charcoal in order to form the required compound of formula (4).

When R represents hydrogen, the imidazole of benzimidazole is protected at position 1 with a suitable N-protecting group, for example a benzyl group, which is subsequently removed, if necessary, using standard procedures.

14) The compounds of formula (4) in which Cy represents a 5-R-isoxazol-4-yl derivative can be prepared by reacting an isoxazole derivative of general formula:

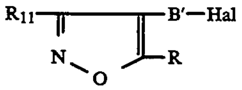

(35)

in which B', R, $R_{11}$ and Hal have the same meaning as above with a 4-methoxy derivative of formula (26) in the presence of a Friedel-Crafts catalyst such as aluminium chloride to form the compounds of general formula:

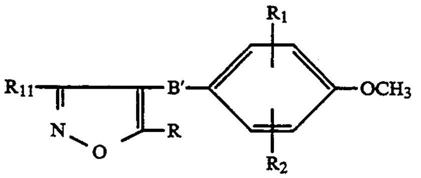

(36)

in which B', R, $R_1$, $R_2$ and $R_{11}$ have the same meaning as above, which compounds are demethylated using aluminium chloride for example to form the required compound of formula (4).

Some compounds of formula (35) are known compounds having been described in Gazz. Chim. Ital. 76, 30 (1946) whereas the other compounds of formula (35) can be prepared in accordance with the method described therein or according to standard methods.

Alternatively, the compounds of formula (36) in which $R_{11}$ represents hydrogen and B' represents a $—SO_2—$ group, can be obtained in accordance with the method described in J. Hetero. Chem. 23, 1363 (1986) by reacting a 1-(4-methoxybenzenesulfonyl)-2-N,N-dimethylaminoethene with hydroxylamine.

Similarly, compounds of formula (36) in which B' represents a $—SO_2—$ group, $R_{11}$ is other than hydrogen and in which $—OCH_3$ is replaced by —O—Tosyl, can be used to form the corresponding compounds of formula (4). These 3-substituted 5-R-4-(4-O-Tosyl) benzenesulfonyl isoxazole derivatives can be prepared in accordance with the method described in Gazz. Chim. Ital. 98, 656 (1968) i.e. by reacting a benzenesulfonylketone and a hydroxamic acid derivative.

15) The compounds of formula (4) in which Cy represents a 5-R-pyrazol-4yl group can be prepared by reacting a compound of general formula:

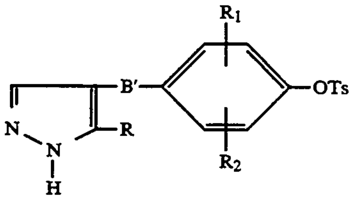

(37)

in which B', R, $R_1$, $R_2$ and Ts have the same meaning as above, with hydrazine in order to form the required compound of formula (4).

The compounds of formula (37) can be obtained in accordance with the method described in J. Hetero. Chem. 23, 1963 (1986), i.e. starting from a N,N-dimethylaminoethene derivative and hydrazine.

Alternatively, the compounds of formula (4) in which Cy represents a 5-R-pyrazol-4-yl group can be obtained directly from a compound of general formula:

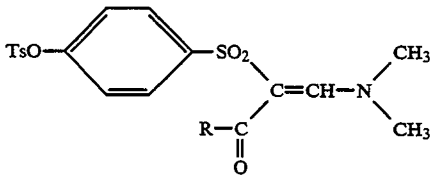

(38)

in which R and Ts have the same meaning as above, and hydrazine in excess.

The compounds of formula (38) can be prepared in accordance with the method described in J. Hetero Chem. 23, 1363 (1986) cited above.

16) The compounds of formula (4) in which Cy represents a 1-$R_9$-2-R -indol-3-yl or a 1-$R_9$-3-R-indol-2-yl can be prepared:

a) when $R_9$ represents hydrogen, by reacting p-methoxythiophenol substituted by $R_1$ and $R_2$ groups, with 2-R-indole or 3-R-indole in the presence of iodine to form an indole derivative of general formula:

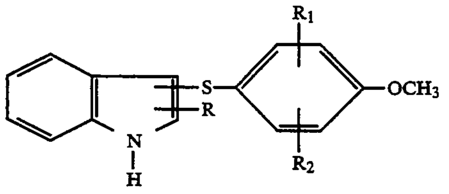

(39)

in which R, $R_1$ and $R_2$ have the same meaning as above, which indole derivative can then be oxidized with 3-chloroperbenzoic acid to form sulfonyl derivatives of general formula:

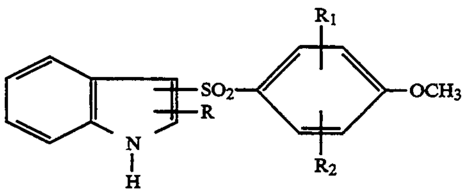

(40)

in which R, $R_1$ and $R_2$ have the same meaning as above. The compounds of formula (39) and (40) can subsequently be demethylated using 2-mercaptoethanol in the presence of sodium hydride to form the required compounds of formula (4).

b) when $R_9$ is other than hydrogen, by treating the compound of formula (39) or (40) with iodide of formula $R_9$—I in which $R_9$ is other than hydrogen and by demethylating the 1-substituted derivative thus obtained by means of 2-mercaptoethanol in the presence of sodium hydride, to form the required compounds of formula (4).

17) The compounds of formula (4) in which Cy represents a 2-R-5-$R_9$-4,5,6,7-tetrahydrothieno [3,2-c]pyrid-3-yl group and B' represents a $—SO_2—$ group can be prepared by reacting a 2-R-5-$R_9$-4,5,6,7-tetrahydrothieno[3,2-c]pyridine in which R9 is other than hydrogen with a compound of general formula:

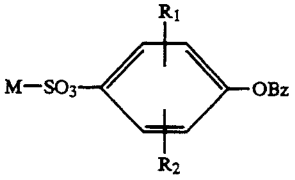
(41)

in which $R_1$, $R_2$, M and Bz have the same meaning as above, in the presence of methanesulfonic acid/-phosphorous pentoxide to form a tetrahydrothienopyridine of general formula:

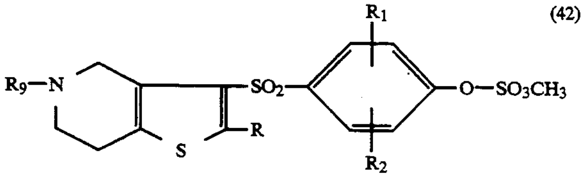
(42)

in which R, $R_1$ and $R_2$ have the same meaning as above and $R_9$ has the same meaning as above with the exception of hydrogen. The compounds of formula (42) are then hydrolysed in the presence of a basic agent such as an alkali metal hydroxide to form the required compounds of formula (4) in which $R_9$ is other than hydrogen.

The starting 2-R-5-$R_9$-4,5,6,7-tetrahydrothieno[3,2-c]pyridines are known compounds having been described in Heterocycles, 22, 1235 (1984) or can be prepared in accordance with the method described therein.

18) The Compounds of formula (4) in which Cy represents a 2-R-thieno [3,2-c]pyrid-3-yl group can be prepared by hydrolying a compound of formula (42) in which $R_9$ represents a benzyl or halogenobenzyl radical, then by reacting the 4-hydroxybenzenesulfonyl derivative thus obtained with palladium on charcoal in diphenylether to form the required compound of formula (4).

19) The compounds of formula (4) in which Cy represents a 5-R-thiazol-4-yl group can be prepared by demethylating a compound of general formula:

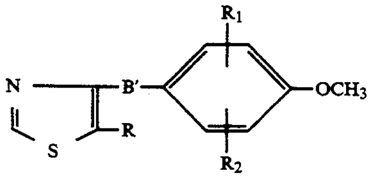
(43)

in which B', R, $R_1$ and $R_2$ have the same meaning as above, using hydrobromic acid in acetic acid to form the required compounds of formula (4).

The compounds of formula (43) can be prepared in accordance with the method described in Tetrah. Lett. 1972, p. 2777 i.e. starting from a sulfonylmethylisonitrile derivative and a thioglycolic acid derivative.

20) The compounds of formula (4) in which Cy represents a 1-$R_9$-5-R-imidazol-4-yl can be prepared by demethylating by means of 2-mercaptoethanol in the presence of sodium hydride a compound of general formula:

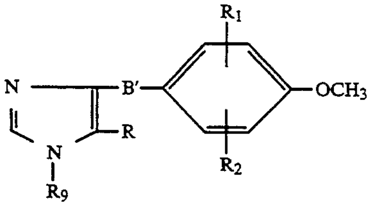
(44)

in which B', R, $R_1$, $R_2$ and $R_9$ have the same meaning as above, to form the required compounds of formula (4).

The compounds of formula (44) can be obtained in accordance with the method described in Tetrahedron Lett. 23, pp. 2373–2374 (1972) i.e. starting from a sulfonylmethylisonitrile and an imidazole derivative.

21) The compounds of formula (4) in which Cy represents an optionally substituted 5-R-oxazol-4-yl derivative can be prepared by treating a benzenesulfonylmethyl formamide derivative of general formula:

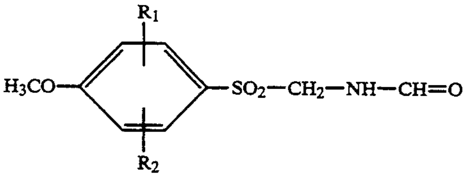
(45)

in which $R_1$ and $R_2$ have the same meaning as above, with phosphorous oxychloride in the presence of an acid acceptor such as triethylamine, to form an isonitrile of general formula:

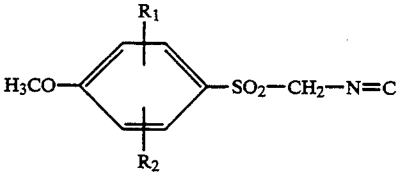
(46)

in which $R_1$ and $R_2$ have the same meaning as above.

This isonitrile is then reacted with an acyl halide of general formula

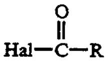
(47)

in which Hal and R have the same meaning as above, to provide the isoxazole derivative of general formula:

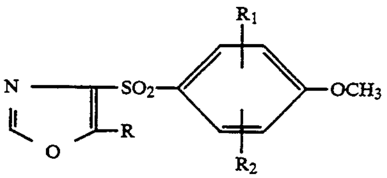
(48)

in which R, $R_1$ and $R_2$ have the same meaning as above, which derivative is demethylated at reflux in the presence of aluminium chloride to form the required compound of formula (4).

22) The compounds of formula (4) in which B' represents a —$SO_2$— group and Cy represents a group of formula (F) in which $R_5$ and $R_6$ are taken together with the carbon atom to which they are attached to form a non-aromatic mono- or bi-cyclic carbocyclic group having from 5 to 10 carbon atoms and optionally substituted by a R group in the α-position with respect to the methyne group, for example a 3-R-inden-2-yl, 2-R-cyclohexen-1-yl or 1-R-3,4-dihydronaphth-2-yl group may be prepared in accordance with the method described in J. Org. Chem. vol. 35, No. 12, pp. 4217–4222 (1970), by heating a compound of general formula:

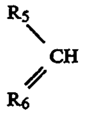
(49)

in which $R_5$ and $R_6$ are taken together with the carbon atom to which they are attached to form a group having from 5 to 10 carbon atoms and optionally substituted by a R group in the α-position with respect to the methyne group, with a halide of 4-tosyloxybenzene substituted by $R_1$ and $R_2$ groups in an appropriate solvent such as benzene and in the presence of anhydrous cupric chloride and triethylamine, to form a 4-tosyloxyphenyl derivative of general formula:

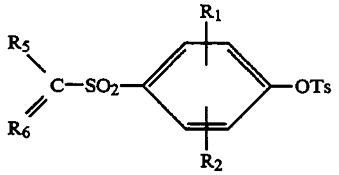
(50)

in which $R_1$, $R_2$ and Ts have the same meaning as above and $R_5$ and $R_6$ have the same meaning as in formula (37), which derivative is then detosylated with a suitable agent such as an alkali metal hydroxide in order to give the required compound of formula (4).

Compounds of formula (4) in which Cy represents a group (G).

The compounds of formula (4) in which Cy represents a 2-R-imidazol-1-yl or a 2-R-benzimidazol-1-yl group can be obtained by reacting a 2-R-imidazole or a 2-R-benzimidazole with a halide of formula (9) in the presence of a Friedel-Crafts catalyst such as aluminium chloride, to form a compound of general formula:

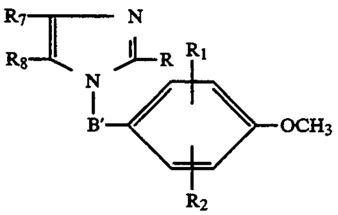
(51)

in which B', R, $R_1$ and $R_2$ have the same meaning as above, which is optionally demethylated using, for example, hydrobromic acid or pyridine hydrochloride, to form the required compound of formula (4 ).

In accordance with another method, the compounds of formula (1), in which B represents a —S— or —$SO_2$— group and A represents an alkylene radical, preferably those in which A represents a propylene radical, can also be obtained by reacting, in the presence of a basic agent such as an alkali metal carbonate, for example potassium carbonate, an alkali metal hydroxide such as sodium or potassium hydroxide, an alkali metal hydride such as sodium hydride or an alkali metal alcoholate, for example sodium methylate or ethylate, a 4-hydroxyphenyl derivative of formula (4) above with a compound of general formula:

X-A-Am (52)

in which X has the same meaning as above and represents preferably chlorine or a benzenesulfonyloxy or p-toluenesulfonyloxy radical, A represents an alkylene radical and Am has the same meaning as above, the reaction taking place at a temperature included between room temperature and the reflux temperature of the medium as well as in a polar solvent such as methyl ethyl ketone or dimethylsulfoxide to form the required aminoalkoxyphenyl derivative of formula (1) in the form of the free base.

When $R_4$ represents hydrogen, the nitrogen atom is preferably protected by a labile group, for example a protecting group which can be removed in basic medium, for example the tert-butoxycarbonyl group (BOC).

The compounds of formula (52) are known compounds or compounds which can be obtained in accordance with known procedures.

The compounds of formula (1) in which Cy represents a group (G), A represents an alkylene chain and B represents a —S— or —$SO_2$— group can also be prepared by reacting a 2-R-imidazole or 2-R-benzimidazole with a halide of general formula:

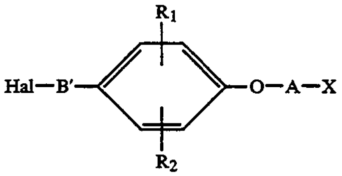
(53)

in which B', $R_1$, $R_2$, Hal and X have the same meaning as above and A represents an alkylene chain, in the presence of an acid acceptor such as triethylamine, to form a compound of general formula:

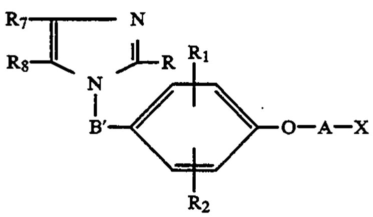
(54)

in which B', R, $R_1$, $R_2$ and X have the same meaning as above, $R_7$ and $R_8$ each represents hydrogen or are taken together with the carbon atom to which they are attached to form a phenyl group and A represents an alkylene chain, which compound is subsequently reacted with an amine of formula (3) to form the required compound of formula (1) in the form of the free base.

Similarly, the compounds of formula (1) in which Cy represents an optionally mono- or di-substituted 2-R-4,5-dihydrofuran-3-yl group, A represents an alkylene chain and B represents a —S— or —$SO_2$— group, can be prepared by hydrolysing a cyclopropane derivative of formula (29) in the presence of an aqueous solution of an alkali metal hydroxide in order to form a 4-methoxyphenyl derivative of general formula:

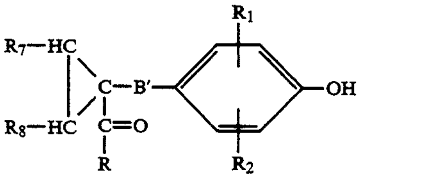

(55)

in which B', R, $R_1$, $R_2$, $R_7$ and $R_8$ have the same meaning as above, which derivative is then reacted:

with a dihaloalkane of formula (5) and the resulting product with an amine of formula (3)

or with a compound of general formula (52) to give an aminoalkoxyphenyl derivative of general formula:

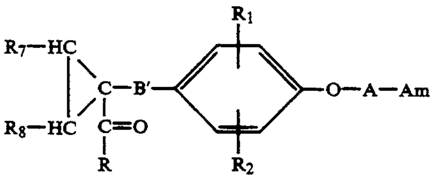

(56)

in which B', R, $R_1$, $R_2$, $R_7$, $R_8$ and Am have the same meaning as above and A represents an alkylene chain. The cyclopropane derivative of formula (56) is then heated to a temperature included between 100° and 130° C. and in the presence of a phase transfer catalyst such as, for example, triphenylphosphine or tricaprylylmethyl ammonium chloride in order to form the required 2,3-dihydrofuran derivative of formula (1) in the form of the free base.

II.—The compounds of formula (1) in which B represents a —SO— group can be obtained by treating a sulfide of formula (1), in which B represents a —S— group, with an oxidizing agent, this compound of formula (1) being in the form of the free base or a salt thereof so as to produce the required compound in the form of the free base or salt.

When the required compound is obtained in the form of a salt, the free base can be regenerated by treatment with a basic agent such as an alkali metal carbonate, for example potassium carbonate, or an alkali metal bicarbonate, for example sodium bicarbonate.

In general, the reaction takes place in water or in an organic solvent such as methylene chloride and in the presence of a suitable oxidizing agent such as for example sodium periodate, potassium permanganate or 3-chloroperbenzoic acid.

Depending on the oxidizing agent used, mixtures of sulfoxides or sulfones can be obtained. These mixtures can be separated by conventional procedures, for example by chromatography.

III.—The compounds of formula (1) in which B represents a —S— or —$SO_2$— group and A represents an optionally substituted 2-hydroxy-propylene chain can be obtained by reacting a 4-hydroxyphenyl derivative of formula (4) at reflux with an epihalohydrin, such as epichlorohydrin or epibromohydrin in the dextrorotatory or laevorotatory form or in the form of a mixture of these isomers, for example in the racemic form and in the presence of a basic agent such as an alkali metal carbonate, for example potassium carbonate, an alkali metal hydroxide, for example sodium or potassium hydroxide, an alkali metal hydride such as sodium hydride or an alkali metal alcoholate, for example sodium methylate or ethylate and in a polar solvent such as methyl ethyl ketone to give the oxiranylmethoxy derivatives of general formula:

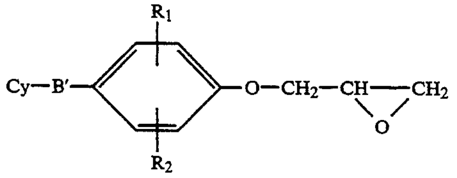

(57)

in which Cy, B', $R_1$ and $R_2$ have the same meaning as above.

The oxiranylmethoxy derivatives of formula (57) are then treated at reflux with an amine of formula (3), this being performed in a polar solvent such as methyl ethyl ketone or in an excess of amine of formula (3) to give the required derivative formula (1) in the form of the free base in which A represents a 2-hydroxypropylene chain, which derivative can be reacted, if desired, with a lower alkyl halide in the presence of a strong base to form the compound of formula (1) in the form of the free base in which A represents a 2-hydroxypropylene chain in which the hydroxy is substituted by a lower alkyl radical.

In some cases, by-products may be formed in parallel with the compounds of formula (57) above, for example 4-(3-halo-2hydroxypropoxy)benzenesulfonyl derivatives.

On reaction with the amine of formula (3), these derivatives will nonetheless give rise to the required compounds of formula (1) in which A represents a 2-hydroxypropylene chain.

The compounds of formula (1) thus obtained in the form of the free base can then be converted into pharmaceutically acceptable salts by reaction with a suitable organic or inorganic acid, for example oxalic, maleic, fumaric, methanesulfonic, benzoic, ascorbic, pamoic, succinic, hexamic, bismethylenesalicylic, ethanedisulfonic, acetic, propionic, tartaric, salicylic, citric, gluconic, lactic, malic, cinnamic, mandelic, citraconic, aspartic, palmitic, stearic, itaconic, glycolic, p-aminobenzoic, glutamic, benzenesulfonic, theophylline acetic acid or with lysine of histidine.

As has been reported in detail by R. CHARLIER in "Bruxelles Medical" No. 9, September 1969, pages 543-560, it is accepted that an anti-angina medication must be capable in particular of antagonizing the cardiovascular reactions of the adrenergic type. For this purpose, agents capable of blocking the α-receptors have been suggested.

However, the clinical application of such compounds to the treatment of angina remained without success, very probably owing to the fact that the antagonists of the α-receptors only induce a very partial neutralization of the adrenergic system, the activity of the β-receptors being unaffected.

Now, the most undesirable haemodynamic symptoms which occur in angina pectoris patients during painful attacks are primarily cardiac, and consequently involve the β-receptors.

In parallel, therapies with β-adrenergic receptor antagonists have been suggested. These compounds, which are of genuine clinical interest, decrease the attacks of angina, by reducing the work of the heart by slowing the heart rate. However, there is no fall in the peripheral arterial resistance which, on the contrary, rises through release of the α-tonus.

However, these drug treatments modify some haemodynamic parameters in a sense which, at a fundamental level, counteracts their beneficial effects for angina pectoris patients in particular and heart patients in general.

If the antiadrenergic aspects of β-blockers is considered, it is clear that only the tachycardia and the increase in the force and the rate of the contraction of the heart are likely to be neutralized, the arterial hypertension resulting from a stimulation of the α-receptors on which β-antagonists have no action.

Now, although the cardiovascular disturbances brought about by the stimulation of the β-receptors are more harmful for angina patients, it nonetheless remains true that arterial hypertension also plays a role which is not insignificant.

Moreover, blocking of the β-receptors involves a risk, depriving the patient suffering from cardiac insufficiency of a compensatory mechanism which he normally brings into play in order to limit his circulatory insufficiency.

This reflex mechanism, the main component of which makes use of the β-adrenergic system results, in particular, in an increase of the force and rate of the contraction of the heart. Consequently, if this system is blocked, the cardiac insufficient patient experiences a worsening of his heart failure. It is hence logical to consider that the use of a β-blocker, the action of which is pure and complete, will always involve a cardiac risk.

Hence, it appears desirable not to look for complete α- or β-antagonist properties, in view of the clinical side effects to which they can give rise. It seems more reasonable to try to lessen rather than to abolish the cardiovascular disturbances which characterize the hyperstimulation of the adrenergic system as a whole.

The compounds of the invention meet this objective since they exhibit incomplete antiadrenergic properties of the α- and β-types. They can thus be considered not as β-blockers but as adrenodecelerators, i.e. partial antagonists of the α and β adrenergic reactions, potentially devoid of the disadvantages listed above for the β-blockers.

Furthermore, the calcium inhibitory component demonstrated in the compounds of the invention will provide a remarkable complement to their cardiovascular pharmacological spectrum.

It is known, in fact, that the transport of calcium ions is one of the essential components of the action potential in heart cells and that, in consequence, it plays a fundamental role in electrical conduction as well as in possible disorders (arrhythmia). Furthermore, it is known that calcium ions are involved in the excitation-contraction coupling which controls the degree of vasoconstriction in smooth muscle and, consequently, plays a critical role in attacks of angina pectoris.

The calcium antagonist compounds act at a level of the cell membrane by selectively preventing calcium from taking part in the contraction process within the arterial cell.

It is presently becoming increasingly obvious that the clinical results obtained with the combination of calcium inhibitors and β-adrenergic inhibitors are better than when each inhibitor is used on its own (J.A.M.A. 1982, 247, pages 1911–1917).

Furthermore, it seems that a β-blocker exerting additionally a significant inhibitory action with respect to calcium transport does not exist at the present time.

From this point of view, the compounds of the invention exhibiting both an anti-calcium component and an α- and β-anti-adrenergic component will be of paramount importance since they are capable of more extensive therapeutic applications than a β-blocker on its own or a calcium inhibitor on its own. As examples, mention should be made of:

1-{4-[3-(6,7-dimethoxy 1,2,3,4-tetrahydro N-isoquinolin-2-yl)propox]benzenesulfony}2-isopropyl indolizine (Ex. 1)

1-{4-[3-(N-methyl N- 6,7-dimethoxy 1,2,3,4-tetrahydro 1-naphthyl amino)propox]benzenesulfonyl}2-isopropyl indolizine (Ex. 13)

However, the major value of these compounds will reside in the fact that, owing to their anti-calcium component, it will be possible to use them in the treatment of angina at rest, a syndrome induced by the appearance of a spasm in the coronary arteries which is combatted at present by compounds such as diltiazem, verapamil or nifedipine.

Moreover, compounds of the invention have been shown to be much less rapidly metabolized in vivo than compounds of the patent FR 2.594,438.

The results of pharmacological tests performed for the purpose of determining the cardiovascular properties of the compounds of the invention are listed below.

I. Calcium inhibitory properties

The inhibitory properties of calcium transport at membranes exhibited by the compounds of the invention were demonstrated by measurement of their antagonistic action to the contractile response to potassium-induced depolarization on isolated rat aorta. It is well established that the depolarization of a smooth muscle membrane by potassium makes the latter permeable to extracellular calcium and induces muscle contraction.

Consequently, the measurement of inhibition of the contractile response to depolarization by potassium or the measurement of relaxation of the tonic contraction on potassium depolarization can provide an evaluation of the potency of a compound as an inhibitor of the membrane permeability to $Ca^{++}$ ions.

The technique used is the following:

The aorta is removed from male Wistar rats weighing about 300 g and cut into strips approximately 40 mm long and 3 mm wide.

These fragments are placed in a 25 ml isolated organ bath containing modified Krebs-bicarbonate solution (112 mM NaCl; 5 mM KCl; 25 mM $NaHCO_3$; 1 mM $KH_2PO_4$; 1.2 mM $MgSO_4$; 2.5 mM $CaCl_2$; 11.5 mM glucose, made up to 1000 ml with distilled water) maintained at 37° C. and through which a stream of carbon dioxide is passed. The preparation is connected to a force microsensor and the contractile response is recorded after amplification on a recorder.

A tension of 2 g is applied to the preparation. This latter is maintained in the modified Krebs-bicarbonate solution for 60 minutes, and then contractions are induced by replacing the Krebs-bicarbonate solution by a Krebs-potassium solution (17 mM NaCl; 100 mM KCl; 25 mM $NaHCO_3$; 1 mM $KH_2PO_4$; 1.2 mM $MgSO_4$; 2.5 mM $CaCl_2$; 11.5 mM glucose; made up to 1000 ml with distilled water). When the contractile response of the preparation has become reproducible, a given amount of the compound of the invention is introduced into the bath. Sixty minutes later a new spasm is induced by potassium depolarization.

The results obtained on the aorta under investigation are then expressed in percent of the maximal contractional effect before incubation with the test substance.

As examples, the following results were obtained, the compounds of formula (1) being in the form of the free base or the oxalate.

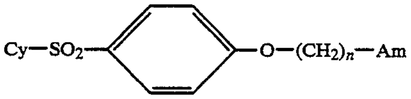

| Compound | Cy | n | Am | % of maximal contractional effect $10^{-6}$M | $10^{-7}$M | $10^{-8}$M | $10^{-9}$ |
|---|---|---|---|---|---|---|---|
| Ex. 1 | 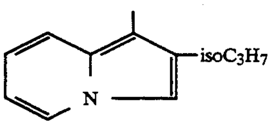 | 3 | 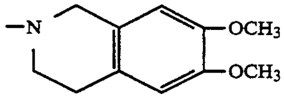 | 9,6 | 18,3 | 72,4 | 92,6 |
| Ex. 7 | 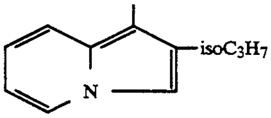 | 4 | 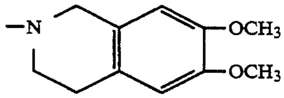 | 8,4 | 31,8 | 82,1 | — |
| Ex. 13 | 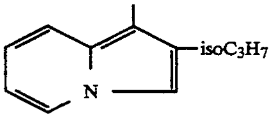 | 3 | 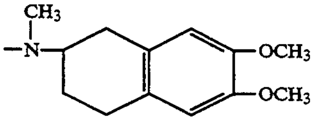 | 4,4 | 13,3 | 61,4 | 87, |
| Ex. 6 | 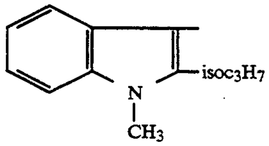 | 3 | 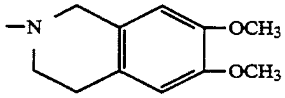 | 10,8 | 47,2 | 89,2 | — |
| Ex. 8 | 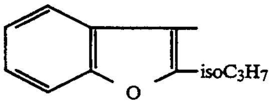 | 3 | 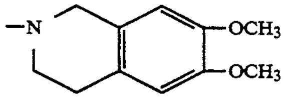 | 9,5 | 35,4 | 65,9 | 81,5 |
| Ex. 10 | 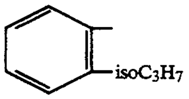 | 3 | 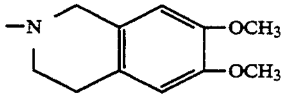 | 1,2 | 44,6 | 81,2 | — |
| Ex. 14 | 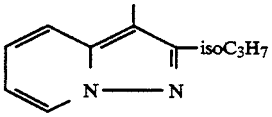 | 3 | 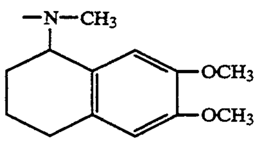 | 16,7 | 25,6 | 78,6 | — |
| Ex. 17 | 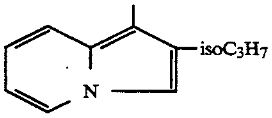 | 3 | 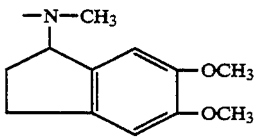 | 6,2 | 8,1 | 50 | 78,7 |

-continued

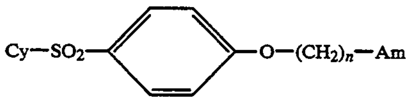

| Compound | Cy | n | Am | % of maximal contractional effect | | | |
|---|---|---|---|---|---|---|---|
| | | | | $10^{-6}$M | $10^{-7}$M | $10^{-8}$M | $10^{-9}$ |
| Ex. 23 | 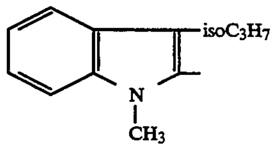 | 3 | 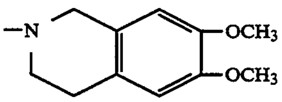 | 23,3 | 37 | 61,9 | 81,7 |

II. Antiadrenergic properties

The aim of this test is to determine the capacity of the compounds of the invention to reduce the increase in blood pressure induced by epinephrine (anti-α effect) and the acceleration of the heart rate induced by isoprenaline (anti-β effect) in the dog previously anesthetized with pentobarbital and atropinized.

First, are determined for each dog the dose of epinephrine (between 3 and 10 μg/kg) which causes a reproducible increase in arterial blood pressure of about $133.10^2$Pa and the dose of isoprenaline (1 to 2 μg/kg) which causes a reproducible increase in the heart rate of about 70 beats/minute. The doses of epinephrine and isoprenaline thus determined are injected alternatively every ten minutes and after the two consecutive reference responses have been obtained, a quantity of the test compound is administered by the intravenous route.

Anti- α effect

The percentage reduction of the hypertension caused by the test compound in comparison with the reference hypertension previously obtained (about 100 mm Hg) is recorded.

Anti-β effect

The percentage reduction of the acceleration of the heart rate caused by the test compound compared with the reference tachycardia previously measured (about 70 beats) is recorded.

In both cases, the results of the reduction in arterial pressure and heart rate are expressed as follows:

+ for a reduction<50%

++ for a reduction≧50%

+++ for an almost complete reduction

The following results were recorded:

| Compounds | Dose (mg/kg) | Anti-α effect | Anti-β effect |
|---|---|---|---|
| Ex. 1 | 0,127 | +++ | ++ |
| Ex. 2 | 0,64 | ++ | ++ |
| Ex. 3 | 1,2 | ++ | ++ |
| Ex. 5 | 2,6 | + | + |
| Ex. 6 | 0,33 | ++ | ++ |
| Ex. 7 | 0,66 | +++ | +++ |
| Ex. 8 | 0,63 | +++ | +++ |
| Ex. 9 | 1,3 | +++ | ++ |
| Ex. 10 | 0,6 | + | + |
| Ex. 12 | 1,2 | +++ | +++ |
| Ex. 13 | 0,34 | +++ | ++ |
| Ex. 14 | 1,2 | +++ | ++ |
| Ex. 17 | 0,11 | +++ | ++ |
| Ex. 18 | 2,8 | ++ | ++ |

-continued

| Compounds | Dose (mg/kg) | Anti-α effect | Anti-β effect |
|---|---|---|---|
| Ex. 23 | 0,068 | +++ | + |

III.—Toxicity

The toxicity of the compounds of the invention is shown to be compatible with their use in therapy.

The therapeutic compositions according to the invention can be made available in any form suitable for administration in human or veterinary medicine. As far as the unit of administration is concerned, it may take the form, for example, of a tablet, a sugar-coated pill, a capsule, a powder, a suspension or a syrup in case of oral administration, a suppository for rectal administration and a solution or suspension for parenteral administration.

The therapeutic compositions of the invention will contain, per administration unit, for example from 50 to 500 mg by weight of active ingredient for oral administration, from 50 to 200 mg of active ingredient for rectal administration and from 50 to 150 mg of active ingredient for parenteral administration.

Depending on the route of administration selected, the therapeutic or veterinary compositions of the invention will be prepared by combining at least one of the compounds of formula (1) or a non-toxic addition salt of this compound with a suitable excipient, this latter being constituted, for example, by at least one ingredient selected from the following substances: lactose, starches, talc, magnesium stearate, polyvinylpyrrolidone, alginic acid, colloidal silica, distilled water, benzyl alcohol or sweetening agents.

The following non-limiting examples illustrate the invention:

EXAMPLE 1

Preparation of 1-{4-[3-(6,7-dimethoxy 1,2,3,4-tetrahydro N-isoquinolin-2-yl)propox]benzenesulfonyl}2-isopropyl indolizine hydrogen oxalate (SR 33710A)

a) 1- 4-(3-bromopropoxy)benzenesulfonyl 2-isopropyl indolizine 3.15 g (0.01 mole) of 1-(4-hydroxybenzenesulfonyl) indolizine, 40.38 g (0.2 mole; 20.3 ml) of 1,3-dibromo propane, 1.66 g (0.012 mole) of potassium carbonate and 20 ml of N,N-dimethylformamide are mixed. The mixture is heated at 100° C. and the reaction is followed by thin layer chromatography (solvent: dichloromethane/ethylacetate 95/5). Reaction is allowed to proceed for 50 minutes, then the excess 1,3-dibromo propane is removed by evaporation under reduced pressure. The residue is taken up in ethyl acetate and washed with diluted sodium hydroxide, then with water. The organic phase is dried over potassium carbonate, then filtered. It is poured into water, extracted with ethylacetate, then washed with water and with a saturated solution of sodium chloride. It is dried over sodium sulfate and concentrated.

In this manner, about 4 g of crude 1-[4-(3-bromopropoxy)benzenesulfonyl]2-isopropyl indolizine are obtained which are recrystallized from an ethyl acetate/hexane mixture. Yield after recrystallization: 67% M.p.: 135.4° C.

1-[4-(4-bromobutoxy)benzenesulfonyl]2-isopropyl indolizine has been prepared in the same manner Yield: 81.5% b) 1{4-[3-(6,7-dimethoxy 1,2,3,4-tetrahydro N-isoquinolin-2-yl)propox]benzenesulfonyl}2-ipopropyl indolizine hydrogen oxalate 1.1 g (0.0025 mole) of 1-[4-(3-bromopropoxy)benzenesulfony]2-isopropyl indolizine, 1.14 g (0.005 mole) of 6,7-dimethoxy 1,2,3,4-tetrahydroisoquinoline hydrocloride and 1.38 g (0.010 mole) of potassium carbonate are mixed at room temperature in 5 ml of dimethylsulfoxide. The mixture is stirred for 22 hours during which the course of the reaction is followed by thin layer chromatography (solvent: methanol), then the reaction product is poured into water. The mixture is extracted with dichloromethane and washed with a saturated aqueous solution of sodium chloride. The extract is dried over sodium sulfate and concentrated in order to obtain about 1.6 g of crude product. It is purified by chromatography on silica gel with an ethylacetate/methanol mixture 80/20 as eluant. 1.05 g of 1-{4-[3-(6,7-dimethoxy 1,2,3,4-tetrahydro N-isoquinolin-2-yl)propox]benzenesulfonyl}2-isopropyl indolizine are recovered in the form of the free base. Yield: 76.5%

1 g (0.0018 mole) of the base thus obtained is then reacted with 0.164 g (0.0018 mole) of oxalic acid in an ethylacetate/ethyl ether mixture.

In this manner, about 0.95 g of 1-{4-[3-(6,7-dimethoxy 1,2,3,4-tetrahydro N-isoquinolin-2-yl)propox]benzenesulfonyl}2-isopropyl indolizine hydrogen oxalate is recovered which can be recrystallized from an ethylacetate/dichloromethane mixture by the addition of ethyl ether. Yield: 83% M.p.: 120°-122° C.

EXAMPLE 2

Preparation of 2-ethyl 3-{4-[3-(6,7-dimethoxy 1,2,3,4-tetrahydro N-isoquinolin2-yl)propox]benzenesulfonyl}benzothiophene hydrogen oxalate (SR 33840A).

A mixture of 4 g (0.0126 mole) of 2-ethyl 3-(4-hydroxy benzenesulfonyl)benzothiophene and 5 g (0.0189mole) of 2-(3-chloropropyl)6,7-dimethoxy 1,2,3,4-tetrahydroisoquinoline is stirred for 3 days in 60 ml of anhydrous dimethylsulfoxide in the presence of 6 g (0.441 mole) of potassium carbonate. After reaction, the mixture is poured into a large volume of water which is extracted 3 times with 100 ml of toluene. The extracts are washed with water, dried over sodium sulfate, filtered and evaporated to dryness in a vacuum. The residue is stirred in heptane and the product formed is recrystallized from ethanol. 3.1 g of product are thus obtained, the oxalate of which is formed in boiling ethylacetate.

In this manner, 3 g of 2-ethyl 3{4-[3-(6,7-dimethoxy 1,2,3,4-tetrahydro N-isoquinolin-2-yl)propox]benzenesulfonyl}benzothiophene hydrogen oxalate are collected after recrystallization from ethanol. Yield: 37% M.p.: 171° C.

EXAMPLE 3

Preparation of 4-{4-[3-(6,7-dimethoxy 1,2,3,4-tetrahydro N-isoquinolin-2-yl)propoxy]benzenesulfonyl}5-isopropyl oxazole hydrogen oxalate (SR 33868A)

a) N-(4-methoxy benzenesulfonylmethyl)formamide.

A suspension composed of 38.85 g (0.2 mole) of sodium 4-methoxy benzenesulfinate, 46.6 ml (0.59 mole) of a 34-37% formaldehyde solution, 90.7 g (2.0 moles) of formamide, 32.5 g (0.707 mole) of formic acid and 100 ml of water are heated for 2 hours at 90°-95° C.

During the reaction the benzenesulfinate gradually dissolves. The mixture is allowed to cool in air, then in an ice bath and the mixture is left to stand in the freezer for about 10 hours. The product which has crystallized is filtered off, washed 3 times with 30 to 35 ml of ice-cold water, then dried at 70° C. in a vacuum.

In this manner, 18.3 g of N-(4-methoxy benzenesulfonylmethyl) formamide are obtained which represents a yield of 39.9% M.p.: 105°-107° C. The filtrate gave a second crop of 1 g, i.e. 2.2% of the required product (M.p.: 105°-107° C.). Total yield: 19.3 g, i.e. 42.1%. Purity: 98.95% b) N-(4-methoxy benzenesulfonyl)methylisonitrile.

The mixture of 16.05 g (0.07 mole) of N-(4-methoxy benzenesulfonylmethyl)formamide, 35 ml of 1,2-dimethoxyethane, 14 ml of isopropyl ether and 35 g (0.35 mole) of triethylamine, cooled to −10° C., is added dropwise, at a temperature between −10° and 0° C., a solution of 11.71 g (0.077 mole) of phosphorus oxychloride in 8.5 ml of 1,2-dimethoxyethane. It is stirred for a further 0.5 hour at about 0° C., then 210 ml of ice-cold water are added dropwise while the temperature is maintained at 0° C. The triethylamine salts dissolve and then an orange-brown precipitate is formed. Stirring is continued for a further 0.5 hour at 0° C., then the precipitate is filtered off and washed with 35 ml of ice-cold water. Cooled N-(4-methoxy benzenesulfonyl)methyl isonitrile which is recrystallized from 50 ml of methanol to give 10.3 g, i.e. a yield of 69.6%. M.p.: 99.5°-101° C.

c) 5-isopropyl 4-(4-methoxy benzenesulfonyl)oxazole.

1.1 g (0.0103 mole) of isobutyryl chloride in 10 ml of 1,2dimethoxyethane is added rapidly at a temperature between 15° and 20° C. to a mixture of 2.1 g (0.01 mole) of 4-methoxy benzenesulfonyl methylisonitrile in 10 ml of 1,2-dimethoxyethane in the presence of 0.65 g (0.0116 mole) of potassium hydroxide. The mixture is stirred for 3 h at about 20° C., cooled in an ice bath and water is added. An oil precipitates which solidifies in the presence of a little methanol. In this manner, 0.45 g of 5-isopropyl 4-(4-methoxy benzenesulfonyl)oxazole is obtained which is recrystallized from 5 ml of isopropanol to give 0.4 g, i.e. a yield of 14.2%. M.p.: 98°-100° C.

d) 4-(4-hydroxybenzenesulfonyl)5-isopropyl oxazole.

A mixture composed of 2.35 g (0.0083 mole) of 5-isopropyl 4-(4-methoxybenzenesulfonyl)oxazole and 4.4 g (0.033 mole) of aluminium chloride is heated at reflux for 6 hours in 58 ml of dichloroethane.

The mixture is poured into 250 ml of water and ice and stirred for 0.5 hour. The organic phase is decanted, washed to neutrality with 2 times 50 ml of water, dried over sodium sulfate and evaporated to dryness in a vacuum. A product precipitates from the aqueous phase, which is added to the residue derived from the organic phase. All of the product is dissolved in methanol and decolorized with 1 mg of active charcoal. The solution is filtered and evaporated. The residue is purified by chromatography on silica with methanol as eluant. After recrystallization from 40 ml of dichloroethane, 0.8 g of 4-(4-hydroxybenzenesulfonyl)5-isoproyl oxazole is obtained which represents a yield of 36.4% M.p.: 196°–198° C.

d) 4-{4-[3-(6,7-dimethoxy 1,2,3,4,-tetrahydro N-isoquinolin-2-yl) propoxy]benzenesulfonyl}5-isopropyl oxazole hydrogen oxalate.

1.35 g (0.005 mole) of 4-(4-hydroxybenzenesulfonyl) 5-isopropyl oxazole and 1.83 g (0.0068 mole) of 2-(3-chloropropyl) 6,7-dimethoxy 1,2,3,4-tetrahydroisoquinoline are mixed at ice bath temperature in 25 ml of dimethylsulfoxide in the presence of 3.45 g (0.025 mole) of potassium carbonate. The temperature is allowed to rise to room temperature and stirring is continued for 4 days. The mixture is poured into 125 ml of ice-cold water and the product which has precipitated is extracted with 25 ml of dichloroethane. The extract is washed with water and decolorized with 0.5 g of active charcoal. It is evaporated to dryness and the residue is recrystallized from 12 ml of isopropanol. 1.3 g of solid is thus obtained which is redissolved in 15 ml of ethanol. 0.27 g of oxalic acid dissolved in 5 ml of methanol is then added. After recrystallization from 20 ml of methanol, 1.4 g of 4-{4[3-(6,7-dimethoxy 1,2,3,4-tetrahydro N-isoquinolin-2-yl)propox]benzenesulfonyl}5-isopropyl oxazole hydrogen oxalate is obtained, i.e. a yield of 55.9%. M.p.: 183°–185° C.

EXAMPLE 4

Preparation of 4-{4- [3-(6,7-dimethoxy 1,2,3,4-tetrahydro N-isoquinolin-2-yl )propox]benzenesulfonyl}5-ethyl 1-methyl pyrazole (SR 33857)

a) 1-(4-tosyloxy benzenesulfonyl)butan-2-one.

A solution composed of 11.65 g (0.035 mole) of sodium 4-tosyloxy benzenesulfinate and 5.2 g (0.035 mole) of 90% 1-bromo butan-2-one in 35 ml of ethanol is heated at reflux for 3 hours. The mixture is allowed to cool and stirred for 2 hours in an ice-water bath. The precipitate is filtered off and washed first with a little ethanol, then 4 times with water.

In this manner, 10.56 g of 1-(4-tosyloxy benzenesulfonyl) butan-2-one are obtained, i.e. a yield of 78.8%. M.p.: 104°–106° C.

1-(4-tosyloxy benzenesulfonyl)3-methyl butan-2-one was prepared by using this same procedure. M.p.: 156°–157° C.

b) 1-(N,N-dimethylamino)1-propionyl 2-(4-tosyloxy benzenesulfonyl) ethene

A mixture composed of 10.25 g (0.027 mole) of 1-(4-tosyloxy benzenesulfonyl)butan-2-one and 8.05 g (0.067 mole) of dimethyl formamide dimethylacetal is heated at reflux for 18 hours in 55 ml of toluene. The mixture is allowed to cool, a light insoluble product is filtered off and the filtrate is evaporated to dryness in a vacuum at 55° C. 13.6 g of a residual oil are thus obtained which are stirred with 30 ml of methanol for 2 h to give 6.7 g of crystalline product.

In this manner, 1-(N,N-dimethylamino)1-propionyl 2-(4-tosyloxy benzenesulfonyl)ethene is obtained in a yield of 57.75%. M.p.: 148°–149.5° C.

1-isobutyryl 1-(4-tosyloxybenzenesulfonyl)2-N,N-dimethylamino ethene was prepared by using this same procedure. Yield: 65.5% Purity: 92.01% M.p.: 115°–116° C.

c) 5-ethyl 4-(4-hydroxybenzenesulfonyl)l-methyl pyrazole.

A mixture composed of 4.3 g (0.01 mole) of 1-(N,N-dimethylamino)-1propionyl 2-(4-tosyloxybenzenesulfonyl)ethene is heated at reflux for 20 hours in 25 ml of methanol and 10 ml of water in the presence of 2.35 g (0.05 mole) of methylhydrazine. The mixture is allowed to cool to room temperature and then cooled in ice for 1 h. It is evaporated to dryness and 4.85 g of residue are thus obtained which are recrystallized from 250 ml of water and decolorized with 0.8 g of active charcoal. The product is filtered off and allowed to crystallize for 2 hours in ice. It is recrystallized again from 50 ml of dichloroethene. In this manner, 1.15 g of 5-ethyl 4-(4-hydroxybenzenesulfonyl)1-methyl pyrazole is obtained which represents a yield of 43.2%. M.p.: 188.5°–190° C.

5-isopropyl 1-methyl 4-(4-hydroxybenzenesulfonyl)-pyrazole is obtained by using this same procedure. Yield: 74.95% M.p.: 209°–210.5° C. Purity: 100% d) 4-{4-[3-(6,7-dimethoxy 1,2,3,4-tetrahydro isoquinolin-2-yl)propoxy]benzenesulfonyl}5-ethyl 1-methyl pyrazole.

This compound was obtained in accordance with the method described in Example 2. M.p.: 120.5°–122° C.

4-{4-[3(6,7-dimethoxy 1,2,3,4-tetrahydro N-isoquinolin-2yl)propox-2-yl)propoxy]benzenesulfonyl}5-isopropyl 1-methyl pyrazole (SR 33849) (Example 5) was prepared in this same manner. Yield: 66.6% M.p.: 90°–92° C.

The following compounds have been prepared using the procedures exemplified above:

3-{4-[3-(6,7-dimethoxy 1,2,3,4-tetrahydro N-isoquinolin-2-yl)propoxy]benzenesulfonyl}2-isopropyl 1-methyl indole oxalate (SR 33837 A) (Example 6). Yield: 26.3% Purity: 98.6% M.p.: 107° C.

1-{4-[4-(6,7-dimethoxy 1,2,3,4-tetrahydro N-isoquinolin-2-yl)butoxy]benzenesulfony}2-isopropyl indolizine hydrogen oxalate (SR 33717A) (Example 7) M.p.: 176.2° C.

2-isopropyl 3-{4-[3-(6,7-dimethoxy 1,2,3,4-tetrahydro N-isoquinolin-2-yl)propox]benzenesulfonyl}benzofuran hydrogen oxalate (SR 33840A) (Example 8) M.p.: 185° C.

2-ethyl 3-{4-[3-(6,7-dimethoxy 1,2,3,4-tetrahydro N-isoquinolin-2-yl)propox]benzenesulfony}benzofuran hydrogen oxalate (SR 33842A) (Example 9) M.p.: 165° C.

4-[2-(6,7-dimethoxy 1,2,3,4-tetrahydro N-isoquinolin-2yl)propox]phenyl (2-isopropyl phenyl)sulfone oxalate (SR 33836A) (Example 10) M.p.: about 106° C.

3-{4-[3-(N-5,6,7,8,9-pentahydrobenzocyclohepten-9-yl N-methyl-amino) propoxy]benzenesulfonyl}2-isopropyl 1-methyl indole hydrogen oxalate (SR 33878A) (Example 11) M.p.: about 76° C.

3-{4-[3-(N-methyl N-1,2,3,4-tetrahydronaphth-1-yl amino) propoxy]benzenesulfonyl}2-isopropyl 1-methyl indole hydrogen oxalate (SR 33874A) (Example 12) M.p.: about 70° C.

1-{4-[3-(N-methyl N-6,7-dimethoxy 1,2,3,4-tetrahydronaphth-2-yl-amino) propoxy]benzenesulfonyl}2-isopropyl indolizine hydrogen oxalate (SR 33739 A) (Example 13). M.p.: 115° C.

3-{4-[3-(N-methyl N-1,2,3,4-tetrahydronaphth-1-yl-amino) propoxy]benzenesulfonyl}2-isopropyl pyrazolo[1,5-a]pyridine hydrogen oxalate (SR 38894 A) (Example 14). M.p.: 99.8° C.

1-methyl 2-{4-[3-(6,7-dimethoxy 1,2,3,4-tetrahydro-N-isoqinolin-2-yl) propoxy]benzenesulfonyl}3-isopropyl indole hydrogen oxalate. (SR 33905 A) (Example 15). M.p.: 116° C. (sinters)

1-methyl 2-{4-[3-(N-methyl N-1,2,3,4-tetrahydronaphth-1-yl-amino) propoxy]benzenesulfonyl}3-methyl indole hydrogen oxalate. (SR 33892 A) (Example 16). M.p.: 101.4° C.

2-Isopropyl 1-{4-[3-(N-methyl N-5,6-dimethoxyindan-1-yl-amino) propoxy}benzenesulfonyl}indolizine (SR 33887) (Example 17). Oily.

4-{4-[3-(N-methyl N-1,2,3,4-tetrahydronaphth-1-yl-amino) propoxy]benzenesulfonyl}5-isopropyl oxazole hydrogen oxalate (SR 33883 A) (Example 18). M.p.: 99.6° C. (isopropanol)

4-{4-[3-( N-methyl N-1, 2,3,4-tetrahydronaphth-1-yl-amino ) propoxy]benzenesulfonyl}5-isopropyl 1-methyl pyrazole hydrogen oxalate. (SR 33899 A) (Example 19). M.p.: 150.7° C. (isopropanol).

4-}4-[3-(N-5,6,7,8,9-pentahydrobenzocyclohepten-9-yl N-methyl-amino) propoxy]benzenesulfonyl}5-isopropyl 1-methyl pyrazole hydrogen oxalate. (SR 33888 A) (Example 20). M.p.: 126.1° C. (ethanol).

2-isopropyl 3-}4-[3-(N-methyl N-1,2,3,4-terahydronaphth-1-yl-amino) propoxy]benzenesulfonyl}benzofuran hydrogen oxalate. (SR 33908 A) (Example 21). M.p.: 113° C. (methyl ethyl ketone)

3-{4-[3-(N-5,6,7,8,9-pentahydrobenzocyclohepten-9-yl N-methyl-amino) propoxy]benzenesulfonyl}2-isopropyl benzofuran hydrogen oxalate. (Example 22) (SR 33913 A) M.p.: 161° C. (ethyl acetate)

1-methyl 2-{4-[3-(6,7-dimethoxy 1,2,3,4-tetrahydro-N-isoquinolin-2-yl) propoxy]benzenesulfonyl}3-isopropyl indole hydrogen fumarate. 5SR 33905 B) (Example 23). M.p.: 177.4° C. (ethanol/ethyl ether).

3-{4-[3-(N-5,6,7,8,9-pentahydrobenzocyclohepten-9-yl N-methyl-amino) propoxy]benzenesulfonyl}2-ethyl benzo[b]thiophene hydrogen oxalate. (SR 33909 A) (Example 24). M.p.: 150° C. (methyl ethyl ketone).

3-{4-[3-(N-methyl N-1,2,3,4-tetrahydronaphth-1-yl-amino) propoxy]benzenesulfonyl}2-ethyl benzo[b]thiophene hydrogen oxalate. (SR 33910 A) (Example 25). M.p.: 167° C. (methyl ethyl ketone).

2-isopropyl 1-{4-[3-(N-7-methoxy 1,2,3,4-tetrahydronaphth-2-yl-amino) propoxy]benzenesulfonyl}indolizine hydrochloride (Example 26). M.p.: 202° C. (isopropanol).

1-methyl 2-phenyl 3-55 4-[3-(6,7-dimethoxy 1,2,3,4-tetrahydro N-isoquinolin-2-yl)propoxy]benzenesulfonyl}indole hydrochloride (Example 27). M.p.: 152° C. (ethyl acetate/ethyl ether)

1-methyl 2-{4-[3-(6,7-dimethoxy 1,2,3,4-tetrahydro N-isoquinolin-2-yl) propoxy]benzenesulfonyl}3-ethyl indole hydrochloride (Example 28).

We claim:

1. An aminoalkoxyphenyl compound corresponding to the formula:

(1)

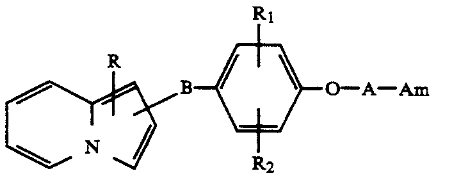

as well as its pharmaceutically acceptable salts in which:

B is selected from —S—, —SO— and —$SO_2$—, $R_1$ and $R_2$, which are identical or different, are selected from the group consisting of hydrogen, methyl, ethyl, and halogen, A is selected from a straight or branched $C_2$-$C_5$ alkylene radical, a 2-hydroxy propylene radical and a 2-($C_1$-$C_4$) alkoxy propylene radical, Am is selected from:

(D)

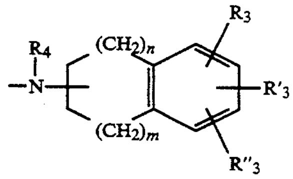

in which: $R_3$, $R'_3$ and $R''_3$, which are identical or different, are selected form the group consisting of hydrogen, halogen, $C_1$-$C_4$ alkyl, $C_1$-$C_4$ alkoxy, $R_4$ is selected from the group consisting of hydrogen and $C_1$-$C_8$ alkyl, n plus m, which are identical or different, are selected from 0,1, and 2, R is in the α-position with respect to the methyne group attached to the group —B— and is selected from hydrogen, $C_1$-$C_8$ alkyl, $C_3$-$C_6$ cycloalkyl, benzyl and phenyl optionally substituted by one or several substituents, which may be identical or different, selected from halogen, $C_1$-$C_4$ alkyl, $C_1$-$C_4$ alkoxy and nitro.

2. A method of treating angina pectoris, hypertension and arrhythmia comprising administering to a patient in need thereof an effective amount of at least one aminoalkoxyphenyl compound of the formula:

(1)

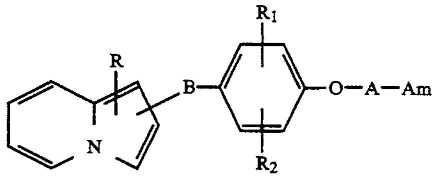

as well as their pharmaceutically acceptable salts in which:

B is selected from —S—, —SO— and —$SO_2$—, $R_1$ and $R_2$, which are identical or different, are selected from the group consisting of hydrogen, methyl, ethyl, and halogen, A is selected from a straight or branched $C_2$-$C_5$ alkylene radical, a 2-hydroxy propylene radical and a 2-($C_1$-$C_4$) alkoxy propylene radical, Am is selected from:

(D)

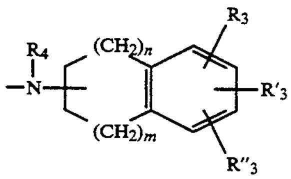

in which: $R_3$, $R'_3$ and $R''_3$which are identical or different, are selected form the group consisting of hydrogen, halogen, $C_1$-$C_4$ alkyl, $C_1$-$C_4$ alkoxy, $R_4$ is selected from the group consisting of hydrogen and $C_1$-$C_8$ alkyl, n plus m, which are identical or different, are selected from 0, 1, and 2, R is in the α-position with respect to the methyne group attached to the group —B— and is selected from hydrogen, C1-$C_8$ alkyl, $C_3$-$C_6$ cycloalkyl, benzyl and phenyl optionally substituted by one or several substituents, which may be identical or different, selected from halogen, $C_1$-$C_4$ alkyl, $C_1$-$C_4$ alkoxy and nitro.

3. A method of reducing or controlling excessive intraocular pressure comprising administering to a patient in need thereof an effective amount of at least one aminoalkoxyphenyl compound of the formula:

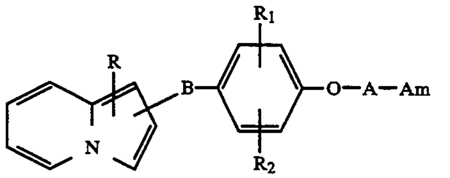
(1)

as well as their pharmaceutically acceptable salts in which:

B is selected from —S—, —SO— and —$SO_2$—, $R_1$ and $R_2$, which are identical or different, are selected from the group consisting of hydrogen, methyl, ethyl, and halogen, A is selected from a straight or branched $C_2$-$C_5$ alkylene radical, a 2-hydroxy propylene radical and a 2—($C_1$-$C_4$) alkoxy propylene radical, Am is selected from:

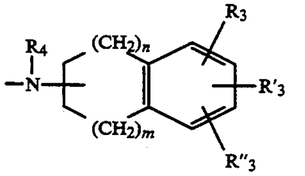
(D)

in which: $R_3$, $R'_3$ and $R''_3$, which are identical or different, are selected form the group consisting of hydrogen, halogen, $C_1$-$C_4$ alkyl, $C_1$-$C_4$ alkoxy, $R_4$ is selected from the group consisting of hydrogen and $C_1$-$C_8$ alkyl, n plus m, which are identical or different, are selected from 0, 1, and 2, R is in the α-position with respect to the methyne group attached to the group —B— and is selected from hydrogen, $C_1$-$C_8$ alkyl, $C_3$-$C_6$ cycloalkyl, benzyl and phenyl optionally substituted by one or several substituents, which may be identical or different, selected from halogen, $C_1$-$C_4$ alkyl, $C_1$-$C_4$ alkoxy and nitro.

4. A method of treating glaucoma comprising administering to a patient in need thereof an effective amount of at least one aminoalkoxyphenyl compound of the formula:

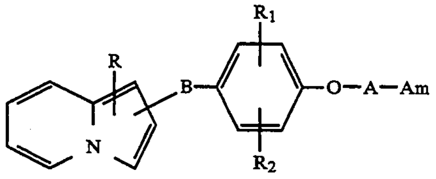
(1)

as well as their pharmaceutically acceptable salts in which:

B is selected from —S—, —SO— and —$SO_2$—, $R_1$ and Rz, which are identical or different, are selected from the group consisting of hydrogen, methyl, ethyl, and halogen, A is selected from a straight or branched $C_2$-$C_5$ alkylene radical, a 2-hydroxy propylene radical and a 2-($C_1$-$C_4$) alkoxy propylene radical, Am is selected from:

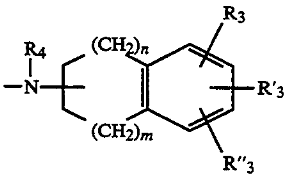
(D)

in which: $R_3$, $R'_3$ and $R''_3$, which are identical or different, are selected form the group consisting of hydrogen, halogen, $C_1$-$C_4$ alkyl, $C_1$-$C_4$ alkoxy, $R_4$ is selected from the group consisting of hydrogen and $C_1$-$C_8$ alkyl, n, plus m, which are identical or different, are selected from 0, 1, and 2, R is in the α-position with respect to the methyne group attached to the group —B— and is selected from hydrogen, $C_1$-$C_8$ alkyl, $C_3$-$C_6$ cycloalkyl, benzyl and phenyl optionally substituted by one or several substituents, which may be identical or different, selected from halogen, $C_1$-$C_4$ alkyl, $C_1$-$C_4$ alkoxy and nitro.

5. A method for the treatment of pathological syndromes of the cardiovascular system in a host in need of such treatment comprising the administration to said host of an effective amount of an aminoalkoxyphenyl derivative according to claim 1.

6. A method for the treatment of ocular diseases in a host in need of such treatment comprising the administration to said host of an effective amount of an aminoalkoxyphenyl derivative according to claim 1.

7. A cycloaminoalkoxyphenyl derivative according to claim 1 in which B represents a —$SO_2$—group.

8. A cycloaminoalkoxyphenyl derivative according to claim 1 in which $R_1$ and $R_2$ each denotes hydrogen.

9. A cycloaminoalkoxyphenyl derivative according to claim 1 in which $R_3$, $R'_3$ and $R''_3$ denote hydrogen or methoxy.

10. A cycloaminoalkoxyphenyl derivative according to claim 1 in which R represents the isopropyl or cyclopropyl group.

11. A cycloaminoalkoxyphenyl derivative according to claim 1 in which the pharmaceutically acceptable salt is the oxalate or the hydrochloride.

12. A cycloaminoalkoxyphenyl derivative according to claim 1 selected from: 1-{4-[3-(N-methyl N-6,7-dimethoxy 1,2,3,4-tetrahydronaphth-2-yl-amino) propoxy]-benzenesulfonyl}2-isopropyl indolizine, 2-isopropyl-1-

{4-[3-(N-methyl-N-5,6-dimethyoxyindan-1-yl-amino) propoxy]benzenesulfonyl}indolizine, and 2-isopropyl-1-{4-[3-(N-7-methoxy-1,2,3,4-tetrahydronaphth-2-yl-amino) propoxy]benzenesulphonyl}indolizine and their pharmaceutically acceptable salts.

13. An aminoalkoxyphenyl compound corresponding to the formula:

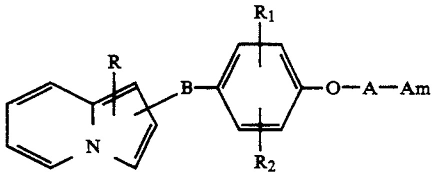

(1)

as well as its pharmaceutically acceptable salts in which:

B is selected from —S—, —SO—, and —$SO_2$—, $R_1$ and $R_2$, which are identical or different, are selected from the group consisting of hydrogen, methyl, ethyl, and halogen, A is selected from a straight or branched $C_2$—$C_5$ alkylene radical, a 2-hydroxy propylene radical and a 2-($C_1$-$C_4$) alkoxy propylene radical, Am is selected from:

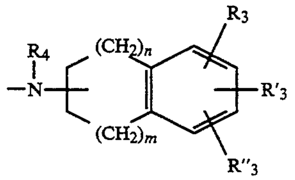

(D)

in which: $R_3$, $R'_3$ and $R''_3$, which are identical or different, are selected from the group consisting of hydrogen, halogen, $C_1$-$C_4$ alkyl, $C_1$-$C_4$ alkoxy, $R_4$ is selected from the group consisting of hydrogen and $C_1$-$C_8$ alkyl, n plus m, which are identical or different, is 2, R is in the α-position with respect to the methyne group attached to the group —B— and is selected from hydrogen, $C_1$-$C_8$ alkyl, $C_3$-$C_6$ cycloalkyl, benzyl and phenyl optionally substituted by one or several substituents, which may be identical or different, selected from halogen, $C_1$-$C_4$ alkyl, $C_1$-$C_4$ alkoxy and nitro.

* * * * *